(12) United States Patent
Bouduban et al.

(10) Patent No.: US 10,265,106 B2
(45) Date of Patent: Apr. 23, 2019

(54) SUTURE DISTAL LOCKING

(71) Applicant: DePuy Synthes Products, Inc., Raynham, MA (US)

(72) Inventors: Nicolas Bouduban, Langendorf (CH); Patrick Burki, Langendorf (CH); Reto Nardini, Langendorf (CH)

(73) Assignee: Depuy Synthes Products, Inc., Raynham, MA (US)

( * ) Notice: Subject to any disclaimer, the term of this patent is extended or adjusted under 35 U.S.C. 154(b) by 0 days.

(21) Appl. No.: 14/446,322

(22) Filed: Jul. 29, 2014

(65) Prior Publication Data

US 2014/0336651 A1 Nov. 13, 2014

Related U.S. Application Data

(62) Division of application No. 13/753,801, filed on Jan. 30, 2013, now Pat. No. 8,821,492.

(60) Provisional application No. 61/597,352, filed on Feb. 10, 2012.

(51) Int. Cl.
*A61B 17/72* (2006.01)
*A61B 17/16* (2006.01)
*A61B 17/17* (2006.01)

(52) U.S. Cl.
CPC ...... *A61B 17/7233* (2013.01); *A61B 17/1615* (2013.01); *A61B 17/1725* (2013.01)

(58) Field of Classification Search
CPC . A61B 17/1615; A61B 17/72; A61B 17/7216; A61B 17/7225; A61B 17/725; A61B 17/7233; A61B 17/1717; A61B 17/1725; A61B 17/1796

USPC .................................................. 606/62–64
See application file for complete search history.

(56) References Cited

U.S. PATENT DOCUMENTS

| | | | | |
|---|---|---|---|---|
| 4,781,181 | A * | 11/1988 | Tanguy | A61B 17/164 606/64 |
| 6,045,551 | A * | 4/2000 | Bonutti | A61B 17/0401 606/215 |
| 6,053,918 | A * | 4/2000 | Spievack | A61B 17/164 606/104 |
| 2011/0218538 | A1* | 9/2011 | Sherman | A61B 17/1631 606/80 |

FOREIGN PATENT DOCUMENTS

| | | |
|---|---|---|
| CN | 201015599 | 2/2008 |
| CN | 101304694 | 11/2008 |
| JP | S62-64356 | 3/1987 |

* cited by examiner

*Primary Examiner* — Julianna N Harvey

(74) *Attorney, Agent, or Firm* — Fay Kaplun & Marcin, LLP

(57) ABSTRACT

A system for locking an intramedullary nail to a bone includes a first plate sized and shaped to be inserted through a channel of an intramedullary nail and dimensioned to prevent its passing through a locking hole of the intramedullary nail and a second plate sized and shaped to be positioned along a portion of an exterior of a hole drilled in the bone and dimensioned to prevent its passing through the hole drilled in the bone along with a connector couplable to the first and second plates and slidable through the channel of the intramedullary nail to extend through the locking hole from an interior of the channel to an exterior of a bone in which the intramedullary nail has been inserted.

19 Claims, 5 Drawing Sheets

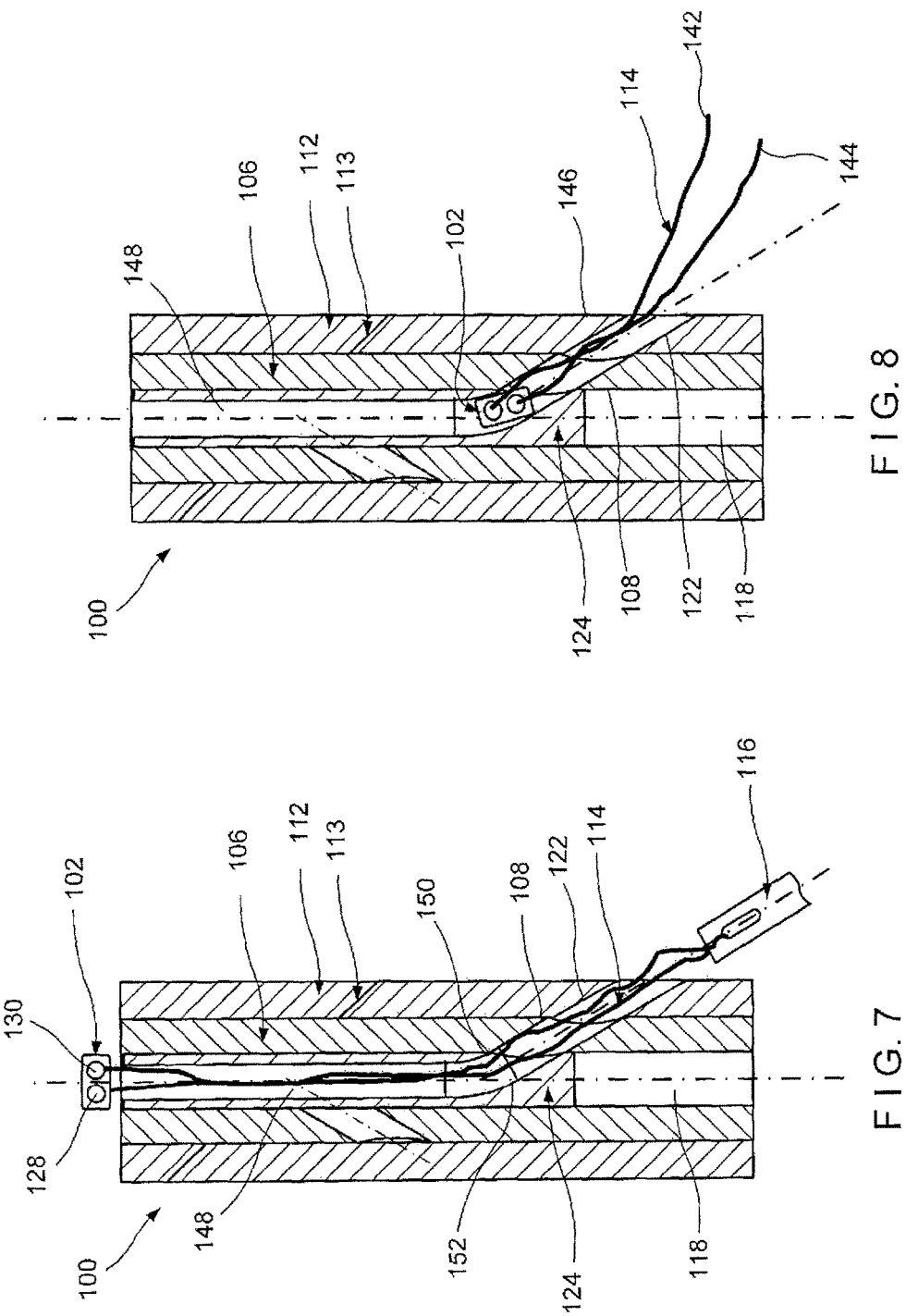

SUTURE DISTAL LOCKING

PRIORITY CLAIM

The present application is a Divisional Application of U.S. patent application Ser. No. 13/753,801 filed on Jan. 30, 2013, now U.S. Pat. No. 8,821,492; which claims priority to U.S. Provisional Patent Application Ser. No. 61/597,352 filed on Feb. 10, 2012. The entire disclosures of these applications/patents are expressly incorporated herein by reference.

BACKGROUND

Intramedullary nails are inserted into medullary canal of long bones to fix fractures thereof and may include locking holes extending laterally through distal and proximal portions thereof to fix the nail to the bone. During insertion, an aiming arm may be attached to a proximal end of an intramedullary nail to aid in locating the positions of the proximal and distal locking holes which are inside the bone and not visible to the surgeon. However, the natural curvature of a medullary canal may cause an intramedullary nail to bend as it is inserted moving the distal locking holes out of alignment with the corresponding holes of an aiming arm.

SUMMARY OF THE INVENTION

The present invention is directed to a system for locking an intramedullary nail to a bone, comprising a first plate sized and shaped to be inserted through a channel of an intramedullary nail and dimensioned to prevent its passing through a locking hole of the intramedullary nail and a second plate sized and shaped to be positioned along a portion of an exterior of a hole drilled in the bone and dimensioned to prevent its passing through the hole drilled in the bone along with a connector couplable to the first and second plates and slidable through the channel of the intramedullary nail to extend through the locking hole from an interior of the channel to an exterior of a bone in which the intramedullary nail has been inserted.

BRIEF DESCRIPTION OF THE DRAWINGS

FIG. 7 shows a longitudinal cross-sectional view of the drill drilling a hole through the bone according to the system of FIG. 1;

FIG. 8 shows a longitudinal cross-sectional view of a first plate positioned within a channel of the intramedullary nail according to the system of FIG. 1;

DETAILED DESCRIPTION

Figure 1:
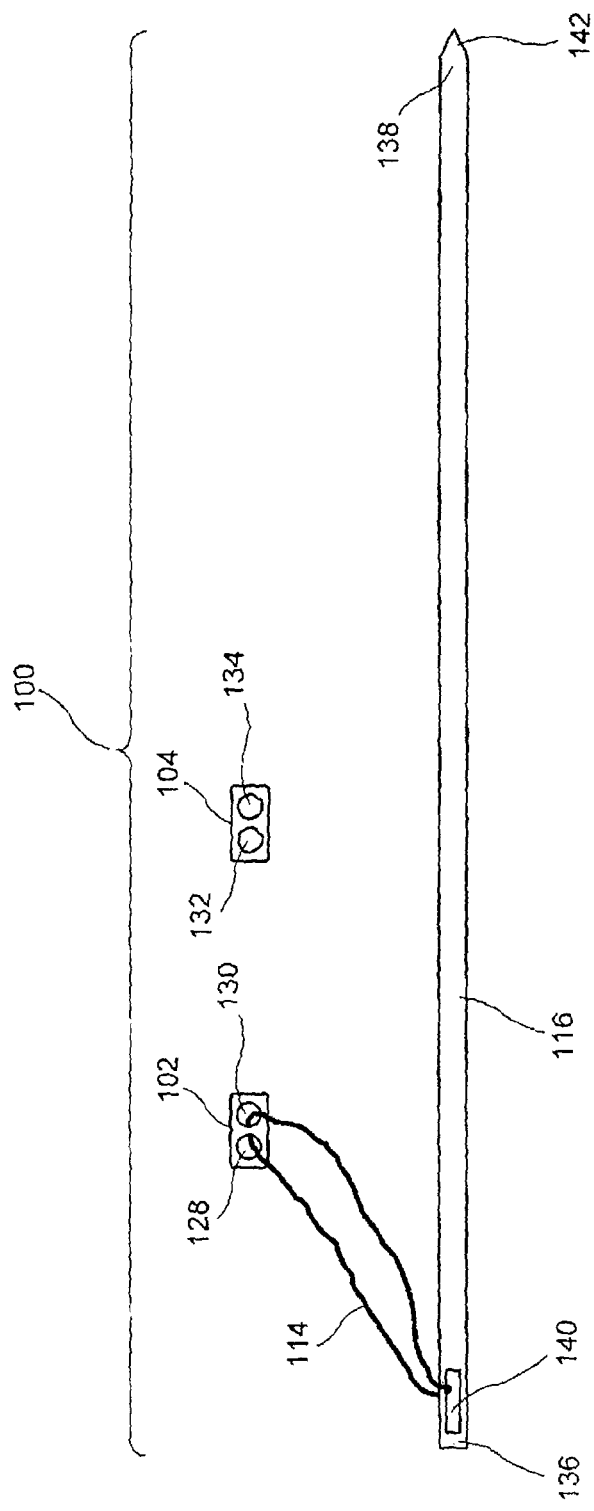
FIG. 1 shows a side view of a system according to an exemplary embodiment of the present invention.

The present invention may be further understood with reference to the following description and the appended drawings, wherein like elements are referred to with the same reference numerals. The present invention relates to a system for treating bone fractures and in particular, a system for providing locking of intramedullary nails. Exemplary embodiments of the present invention describe a pair of plates and a connector which may be passed through a locking hole to fix an intramedullary nail to a bone. It should be noted that the terms "proximal" and "distal," as used herein, are intended to refer to a direction toward (proximal) and away from (distal) a user of the device.

As shown in FIGS. 1-10, a system 100 according to an exemplary embodiment of the present invention comprises a first plate 102 and a second plate 104 for fixing an intramedullary nail 106 to a bone 112 via a connector 114 passing through a distal locking hole 108 of the nail 106. As described in more detail below, the first plate 102 is positioned outside the bone while the second plate 104 is within the intramedullary nail with the two plates 102, 104 affixed on opposite sides of the distal locking hole 108 and affixed to one another via the connector 114, which passes through the distal locking hole 108 and a corresponding hole 122 in the bone 112, to fix the intramedullary nail 106 at a desired position within the bone 112. The system 100 further comprises a flexible drill 116 for threading the connector 114 and the first plate 102 through a channel 118 of the nail 106 to the distal locking hole 108 and for drilling a hole 122 into the bone 112 aligned with the distal locking hole 108. The system 100 may also comprise a drill guide 124 for guiding the flexible drill 116 through the laterally extending distal locking hole 108.

Figure 2:
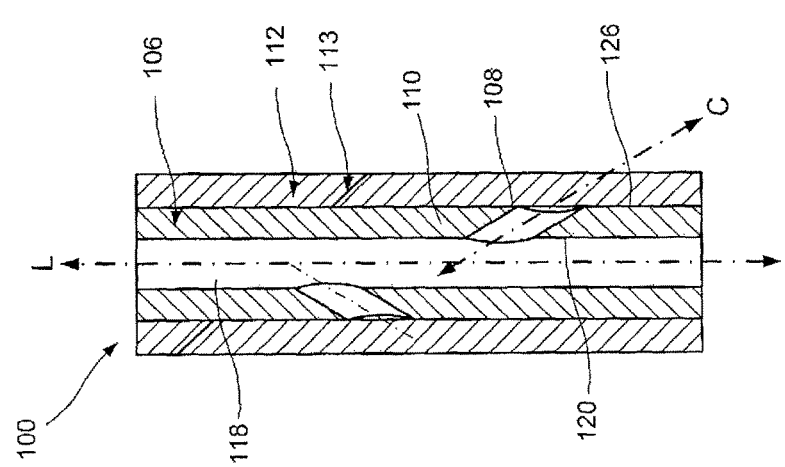
FIG. 2 shows a longitudinal cross-sectional view of a portion of an intramedullary nail inserted into a bone according to the exemplary embodiment of the system of FIG. 1.

As shown in FIG. 2, the intramedullary nail 106 is sized and shaped to be inserted into a medullary canal of a bone 112 to fix a fracture 113 thereof. The channel 118 extends through the intramedullary nail 106 along a longitudinal axis L thereof and the distal locking hole 108 extends laterally through the wall 110 of a distal portion thereof from an interior 120 of the channel 118 to an exterior 126 of the nail 106. A central axis C of the distal locking hole 108 may extend through the wall 110 at an acute angle with respect to a longitudinal axis L of the intramedullary nail 106 such that the locking hole 108 extends from the interior 120 to the exterior 126 of the wall 110 toward a distal end of the intramedullary nail 106. Although the exemplary embodiment describes a single distal locking hole 108, it will be understood by those of skill in the art that the intramedullary nail 106 may include a plurality of distal locking holes 108. Where the intramedullary nail 106 includes a plurality of distal locking holes 108, each of the locking holes 108 may extend through the wall 110 at varying positions about and along the nail 106. It will also be understood by those of skill in the art that although the exemplary embodiment describes a system 100 for distal locking of the intramedullary nail, the system of the present invention may also be used to lock the intramedullary nail to bone via proximal locking holes.

As shown in FIGS. 7-10, the first and second plates 102, 104 are sized and shaped so that, in a first orientation they may be inserted through the channel 118 of the intramedullary nail 106 but, in a second orientation (when oriented transverse to a locking hole 108), the plates 102, 104 contact edges of the locking holes 108 and are prevented from passing therethrough. The first and second plates 102, 104 include first openings 128, 132, respectively, and second openings 130, 134, respectively, extending therethrough similarly to a button. The first and second openings 128, 130, 132, 134 of the first and second plates 102, 104 are sized and shaped to permit the connector 114 to be threaded therethrough. The connector 114 may be any connector suitable for flexibly connecting the first and second plates 102, 104 together. It will be appreciated by those skilled in the art that the thread-like connector 114 may be any element suitable to flexibly connect the first and second plates 102, 104 to one another including, for example, a suture, a shortening joining element such as the joining element described in U.S. Patent Application Publication No. 2008/281355, which is hereby incorporated by reference in its entirety, and a flexible wire such as a cerclage wire. As will be described in greater detail below, the first and second plates 102, 104 are positioned on opposite sides of the distal locking hole 108 and attached to one another via the connector 114 to fix the intramedullary nail 106 to the bone 112.

As shown in FIG. 1, the drill 116 extends longitudinally from a proximal end 136 to a distal end 138 and is flexible along a length thereof. The proximal end 136 includes an eyelet 140 extending laterally therethrough such that the connector 114 may be threaded therethrough, similarly to a thread and needle. The connector 114 is threaded through the eyelet 140 to attach the first plate 102 thereto by threading the connector 114 through the first and second openings 128, 130 thereof to form a closed loop with the connector 114 by tying and/or knotting ends thereof. The distal end 138 includes a drill tip 142 configured to facilitate drilling of the hole 122 through the bone 112 as would be understood by those skilled in the art. The drill 116 may be formed of any of a variety of flexible materials suitable for drilling through bone such as, for example, nitinol, gum metal and PEEK.

The drill guide 124, as shown in FIGS. 3-6, includes a shaft 154 extending from a proximal end 156 to a distal end 158, the shaft 154 being sized and shaped for insertion through the channel 118 of the intramedullary nail 106. The proximal end 156 includes an end member 160 couplable with a proximal end 107 of the intramedullary nail 106. The drill guide 124 includes a lumen 148 extending through the end member 160 and at least a portion of a length of the shaft 154 along with a slot 150 extending laterally therethrough in communication with a distal end of the lumen 148. The lumen 148 is sized and shaped to permit the drill 116 and the first plate 102 to be slid therethrough.

Figure 6:
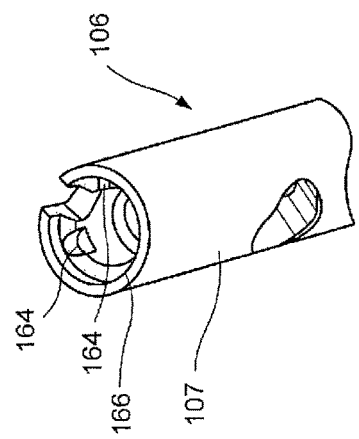
FIG. 6 shows a perspective view of a proximal end of the intramedullary nail according to the system of FIG. 1.
Figure 5:
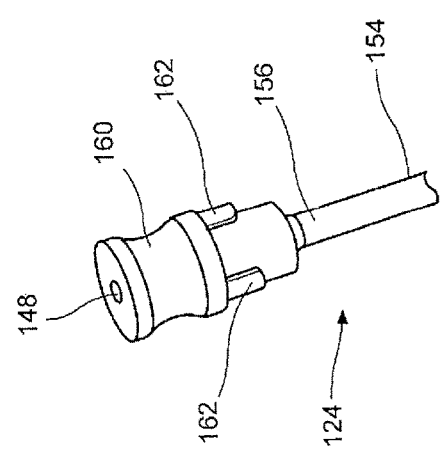
FIG. 5 shows a perspective view of a proximal end of the drill guide of FIG. 4.

The end member 160 and the proximal end 107 of the intramedullary nail 106 are couplable to one another such that the slot 150 is aligned with the distal locking hole 108. For example the end member 160, as shown in FIG. 6, includes a protrusion 162 extending radially outward from a portion thereof to engage a corresponding recess 164, as shown in FIG. 7, along an inner surface 166 of the proximal end 107 of the intramedullary nail 106. Thus, when the protrusion 162 and the recess 164 engage one another, the slot 154 is aligned with the distal locking hole 108. It will be understood by those of skill in the art that the end member 160 and the intramedullary nail 106 may include more than one protrusion 162 and recess 164, respectively. A length of the shaft 154 may be selected such that when the end member 160 is coupled with the proximal end 107 of the intramedullary nail 106, the slot 150 is aligned with the distal locking hole 108. The lumen 148 includes a ramped surface 152 substantially opposing the slot 150 such that when the drill 116 is slid therethrough, the distal end 138 of the drill 116 contacts the ramped surface 152 and is guided laterally out of the slot 150. Thus, the end member 160 is coupled to the intramedullary nail 106 so that the shaft 154 is inserted into the channel 118 and positioned therein such that the slot 150 is in alignment with the distal locking hole 108 to guide the drill 116 therethrough.

Figure 3:
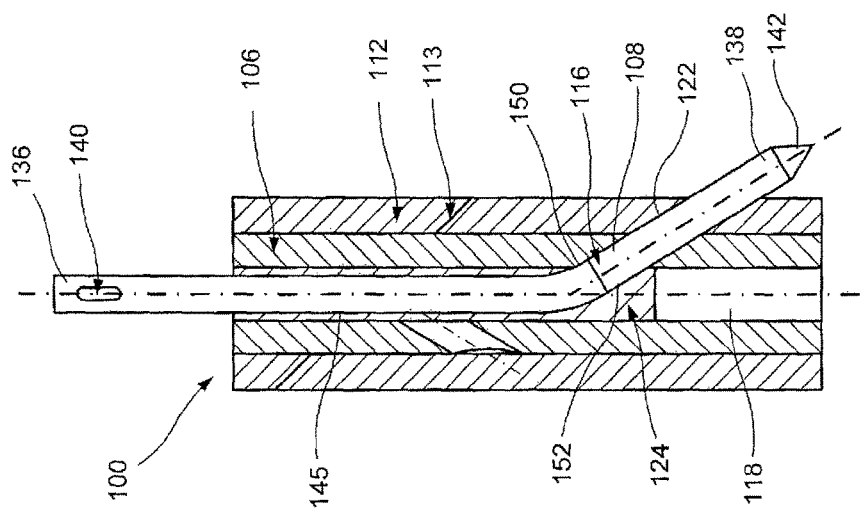
FIG. 3 shows a longitudinal cross-sectional view of a drill inserted through the intramedullary nail according to the system of FIG. 1.
Figure 4:
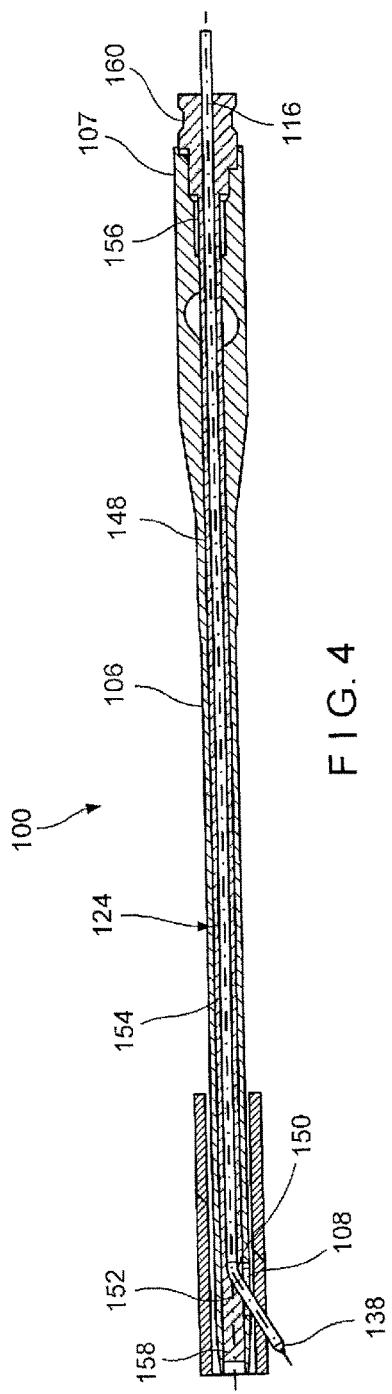
FIG. 4 shows a longitudinal cross-sectional view of a drill guide and drill inserted through the intramedullary nail according to the system of FIG. 1.

According to an exemplary surgical technique using the system 100, the intramedullary nail 106 is inserted along the medullary canal of the bone 112 to fix a fracture thereof, as shown in FIG. 2. The connector 114 may be threaded through the eyelet 140 of the drill 116, inserted through first and second openings 128, 130 of the first plate 102 and tied to form a closed loop, as shown in FIG. 1. It will be apparent to those skilled in the art, however, that other ways of connecting the first plate 102 to the drill 140 are also possible. For example, the connector 114 may be pre-arranged or pre-connected to the eyelet 140. The shaft 154 of the drill guide 124 is inserted into the channel 118 and the end member 160 coupled to the proximal end 107 of the intramedullary nail 106 such that the slot 150 is aligned with the distal locking hole 108. The drill 116, with the connector 114 and first plate 102 assembled therewith, are then inserted through the lumen 148 of the drill guide 124, as shown in FIGS. 3 and 4. The drill 116 is slid along the lumen 148 until the distal end 138 comes into contact with the ramped surface 152 and is deflected laterally out of the distal locking hole 108 with which it is aligned. As the distal end 138 passes through the locking hole 108, the drill is rotated so that the drill tip 142 drills a hole 122 into the bone 112 in alignment with the distal locking hole 108. The drill 116 is passed to the exterior 146 of the bone 112, as shown in FIG. 7, until the first plate 108 contacts the interior 120 of the wall 110 surrounding the distal locking hole 108, as shown in FIG. 8.

Figure 9:
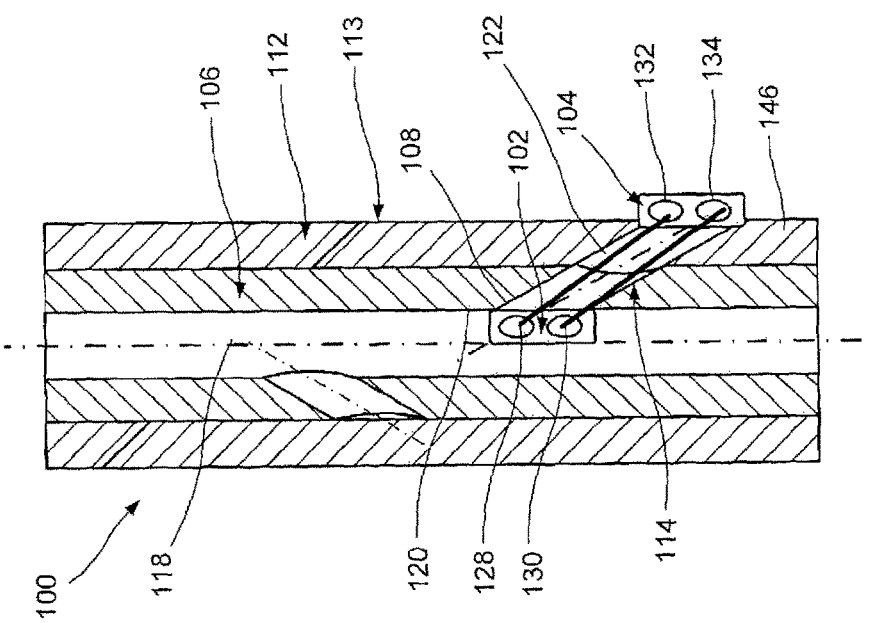
FIG. 9 shows a longitudinal cross-sectional view of first and second plates fixing the intramedullary nail to the bone according to the system of FIG. 1.
Figure 10:
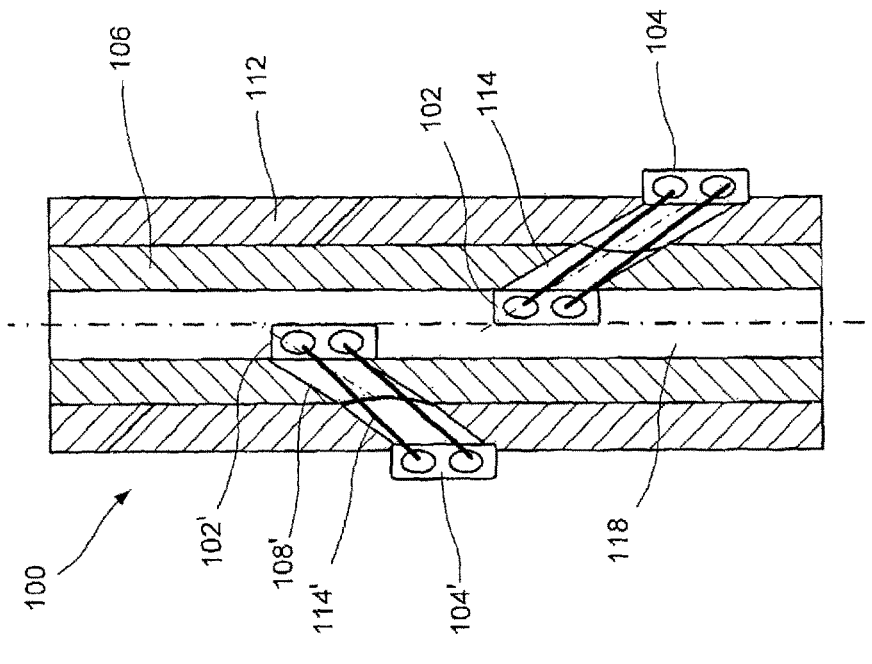
FIG. 10 shows a longitudinal cross-sectional view of a second set of plate fixing the intramedullary nail to the bone according to the system of FIG. 1.

The drill guide 124 is then removed from the intramedullary nail 106 and the drill 116 is detached from the first plate 102 by cutting the connector 114 to form two loose ends 142, 144, which are then used to attach the second plate 104 to the exterior 146 of the bone 112. In particular, the first loose end 142 is threaded through the first opening 132 of the second plate 104 and the second loose end 144 is threaded through the second opening 134 of the second plate 104. The two loose ends 142, 144 are then tied/knotted, applying a tension to the connector 114 and affixing the second plate 104 to the exterior 146 of the bone 112 surrounding the hole 122. Thus, as shown in FIG. 9, the first and second plates 102, 104 are attached to one another via the connector 114 from the interior 120 of the channel 118 to the exterior 146 of the bone 112 such that the intramedullary nail 106 is fixed to the bone 112. The above described steps may be repeated using additional plates 102', 104' and connectors 114' to fix the intramedullary nail 106 to the bone 112 via any additional locking holes 108' of the intramedullary nail 106, as shown in FIG. 10.

It will be apparent to those skilled in the art that various modifications and variations can be made in the structure and the methodology of the present invention, without departing from the spirit or scope of the invention. Thus, it is intended that the present invention cover the modifications and variations of this invention provided that they come within the scope of the appended claims and their equivalents.

What is claimed is:

1. A system for locking an intramedullary nail to a bone, comprising:
   a first plate sized and shaped to be inserted through a channel of an intramedullary nail and dimensioned to prevent its passing through a locking hole of the intramedullary nail;
   a second plate sized and shaped to be positioned along a portion of an exterior of a hole drilled in the bone and dimensioned to prevent its passing through the hole drilled in the bone;
   a connector couplable to the first and second plates and slidable through the channel of the intramedullary nail to extend through the locking hole from an interior of the channel to an exterior of a bone in which the intramedullary nail has been inserted; and
   a flexible drill sized and shaped for insertion through the channel of the intramedullary nail to drill the hole in the bone in alignment with the locking hole, the flexible drill extending from a proximal end to a bone-drilling distal end along a longitudinal axis, the proximal end including a coupling element extending through the flexible drill transverse to the longitudinal axis for receiving the connector for coupling the first plate to the proximal end of the flexible drill.

2. The system of claim 1, wherein the first plate has a dimension selected to prevent the passing of the first plate through a locking hole of the intramedullary nail when in a transverse orientation relative to the locking hole.

3. The system of claim 1, wherein the second plate is sized and shaped to be positioned along a portion of an exterior of a hole drilled in the bone in alignment with the locking hole, the second plate including a connecting portion for coupling the second plate to the connector.

4. The system of claim 1, wherein the connector is thread-like and each of the first and second plates has at least a first opening through which the connector is positioned to couple the first and second plates together.

5. The system of claim 1, wherein, in an initial configuration, the connector is coupled to the first plate and couplable to the second plate.

6. The system of claim 1, wherein the connector is thread-like and the coupling element is an eyelet sized and shaped to permit the connector to be threaded therethrough for forming a closed loop with the first plate, when the first plate is coupled to the connector.

7. The system of claim 1, wherein the flexible drill comprises one of or is any combination of nitinol, gum metal, titanium, sprung steel, magnesium and PEEK.

8. The system of claim 1, further comprising a drill guide sized and shaped for insertion through the channel of the intramedullary nail, the drill guide including a lumen extending longitudinally therethrough and a slot extending laterally therethrough in communication with the lumen.

9. The system of claim 8, wherein the lumen of the drill guide includes a ramped surface opposing the slot such that a drill inserted distally through the lumen contacts the ramped surface and is guided laterally through the slot.

10. The system of claim 8, wherein the drill guide includes a proximal end member couplable to a proximal end of the intramedullary nail such that the slot is aligned with the locking hole of the intramedullary nail.

11. A system for treating a bone, comprising:
    an intramedullary nail extending from a proximal end to a distal end, the nail including a channel extending therethrough and a locking hole extending laterally therethrough from an interior of the channel to an exterior thereof;
    a first plate sized and shaped to be inserted through the channel but prevented from passing through the locking hole, the first plate including a first opening and a second opening extending therethrough;
    a connector coupled to the first plate and slidable through the channel of the intramedullary nail to extend through the locking hole from an interior of the channel to an exterior of a bone in which the intramedullary nail has been inserted such that the first plate, when in an operative configuration, is positioned along a portion of the interior of the channel surrounding the locking hole;
    a second plate sized and shaped to be positioned along a portion of an exterior of a hole drilled in the bone in alignment with the locking hole, the second plate including a coupling element to which the connector is couplable to fix the first and second plates to one another; and
    a flexible drill sized and shaped for insertion through the channel of the intramedullary nail to drill the hole in the bone in alignment with the locking hole, the flexible drill extending from a proximal end to a bone-drilling distal end along a longitudinal axis, the proximal end including a coupling element extending through the flexible drill transverse to the longitudinal axis for receiving the connector for coupling the first plate to the proximal end of the flexible drill.

12. The system of claim 11, wherein the connector is thread-like and the second plate comprises at least a first opening for receiving the connector to couple the connector thereto.

13. The system of claim 11, wherein the connector is thread-like and the first plate includes at least a first opening for receiving the connector to couple the connector thereto.

14. The system of claim 11, wherein a central axis of the locking hole extends at an acute angle relative to a longitudinal axis of the intramedullary nail.

15. The system of claim 11, wherein the connector is thread-like and the coupling element is an eyelet sized and shaped to permit the connector to be threaded therethrough for forming a closed loop with the first plate, when the first plate is coupled to the connector.

16. The system of claim 11, further comprising a drill guide sized and shaped for insertion through the channel of the intramedullary nail, the drill guide including a lumen extending longitudinally therethrough and a slot extending laterally therethrough in communication with the lumen, the lumen sized and shaped to permit the flexible drill to be slid therethrough.

17. The system of claim 16, wherein the lumen of the drill guide includes a ramped surface opposing the slot such that the drill, when inserted distally therethrough, contacts the ramped surface and is guided laterally through the slot.

18. The system of claim 17, wherein the drill guide includes a proximal end member couplable to a proximal end of the intramedullary nail such that the slot is aligned with the locking hole of the intramedullary nail.

19. The system of claim 11, wherein the flexible drill comprises one of or is any combination of nitinol, gum metal, titanium, spring steel, magnesium and PEEK.

\* \* \* \* \*